(12) United States Patent
Lechner et al.

(10) Patent No.: US 10,219,994 B2
(45) Date of Patent: Mar. 5, 2019

(54) METHOD FOR THE SIMULTANEOUS PERMANENT SHAPING AND DYEING OF KERATINIC FIBERS

(71) Applicant: Henkel AG & Co. KGaA, Düsseldorf (DE)

(72) Inventors: Torsten Lechner, Düsseldorf (DE); Yvonne Lissner, Hamburg (DE); Birgit Rautenberg-Groth, Ellerau (DE)

(73) Assignee: Henkel AG & Co. KGaA (DE)

( * ) Notice: Subject to any disclaimer, the term of this patent is extended or adjusted under 35 U.S.C. 154(b) by 15 days.

(21) Appl. No.: 15/487,829

(22) Filed: Apr. 14, 2017

(65) Prior Publication Data

US 2017/0252291 A1    Sep. 7, 2017

Related U.S. Application Data

(63) Continuation of application No. PCT/EP2015/070358, filed on Sep. 7, 2015.

(30) Foreign Application Priority Data

Oct. 15, 2014    (DE) .................. 10 2014 220 916

(51) Int. Cl.

| | | |
|---|---|---|
| *A61K 8/24* | (2006.01) | |
| *A61K 8/23* | (2006.01) | |
| *A61K 8/22* | (2006.01) | |
| *A61K 8/19* | (2006.01) | |
| *A45D 7/04* | (2006.01) | |
| *A61K 8/97* | (2017.01) | |
| *A61K 8/44* | (2006.01) | |
| *A61Q 5/04* | (2006.01) | |
| *A61Q 5/06* | (2006.01) | |
| *A61Q 5/10* | (2006.01) | |
| *A61K 8/29* | (2006.01) | |
| *A61K 8/31* | (2006.01) | |
| *A61K 8/34* | (2006.01) | |
| *A61K 8/36* | (2006.01) | |
| *A61K 8/368* | (2006.01) | |
| *A61K 8/37* | (2006.01) | |
| *A61K 8/41* | (2006.01) | |
| *A61K 8/46* | (2006.01) | |
| *A61K 8/49* | (2006.01) | |
| *A61K 8/55* | (2006.01) | |

(Continued)

(52) U.S. Cl.

CPC .................. *A61K 8/97* (2013.01); *A45D 7/04* (2013.01); *A61K 8/19* (2013.01); *A61K 8/22* (2013.01); *A61K 8/23* (2013.01); *A61K 8/24* (2013.01); *A61K 8/29* (2013.01); *A61K 8/31* (2013.01); *A61K 8/342* (2013.01); *A61K 8/345* (2013.01); *A61K 8/347* (2013.01); *A61K 8/361* (2013.01); *A61K 8/368* (2013.01); *A61K 8/375* (2013.01); *A61K 8/41* (2013.01); *A61K 8/411* (2013.01); *A61K 8/44* (2013.01); *A61K 8/447* (2013.01); *A61K 8/46* (2013.01); *A61K 8/463* (2013.01); *A61K 8/4926* (2013.01); *A61K 8/55* (2013.01); *A61K 8/553* (2013.01); *A61K 8/60* (2013.01); *A61K 8/645* (2013.01); *A61K 8/73* (2013.01); *A61K 8/731* (2013.01); *A61K 8/817* (2013.01); *A61K 8/8141* (2013.01); *A61Q 5/04* (2013.01); *A61Q 5/065* (2013.01); *A61Q 5/10* (2013.01); *A45D 2/00* (2013.01); *A45D 2007/001* (2013.01); *A61K 2800/4322* (2013.01); *A61K 2800/884* (2013.01)

(58) Field of Classification Search

CPC . A61Q 5/04; A61Q 5/10; A45D 7/045; A45D 7/075; A61K 8/97

See application file for complete search history.

(56) References Cited

U.S. PATENT DOCUMENTS

| | | | |
|---|---|---|---|
| 4,630,621 A | | 12/1986 | Pontani |
| 5,161,553 A | * | 11/1992 | Cohen ...................... A61K 8/02 132/205 |

(Continued)

FOREIGN PATENT DOCUMENTS

| | | | | |
|---|---|---|---|---|
| DE | 19713698 C1 | | 6/1998 | |
| EP | 0083095 A2 | * | 7/1983 | ............... A61K 8/23 |

(Continued)

OTHER PUBLICATIONS

Rastogi et al., Precursors of oxidative hair dyes in hair colouring formulations, National Environmental Research Institute, Denmark 25pp (2003).*
Draelos, Cosmetics and Dermatological Problems and Solutions, 3rd Ed, Informa Healthcare, CRC Press, Florida, p. 186 (2011).*
McMillan-Bodell, Introducing Hairdressing, Heinemann Educational Publishers, Oxford, p. 96 (2004).*
Mueller et al., EP 1797865, EPO Machine translation of non-English application downloaded Feb. 7, 2018 (Year: 2007).*

(Continued)

*Primary Examiner* — Alma Pipic
(74) *Attorney, Agent, or Firm* — James J. Cummings

(57) ABSTRACT

A method for the permanent shaping and color modification of keratinic in a single process includes the following steps. First, an aqueous composition, including at least one keratin-reducing compound and at least one alkalizing agent, is applied to the keratinic fibers and is left on the keratinic fibers for a period of 5 to 50 minutes at a temperature of 20 to 45° C. The keratinic fibers are rinsed, and optionally dried. Next, a composition including at least one oxidation dye precursor and at least one oxidizing agent is applied to the keratinic fibers and the keratinic fibers are deformed. That composition is allowed to act for 10 to 35 minutes. An aqueous composition including at least one oxidizing agent, is applied to the keratinic fibers for 30 seconds to 15 minutes. The keratinic fibers are rinsed out, along with removal of the deformation aids.

20 Claims, No Drawings

(51) Int. Cl.
    *A61K 8/60*         (2006.01)
    *A61K 8/64*         (2006.01)
    *A61K 8/73*         (2006.01)
    *A61K 8/81*         (2006.01)
    A45D 2/00         (2006.01)
    A45D 7/00         (2006.01)

(56) References Cited

U.S. PATENT DOCUMENTS

| 5,340,367 | A | | 8/1994 | Schultz et al. |
| 5,942,009 | A | * | 8/1999 | Burns ..................... A61K 8/64 |
| | | | | 132/204 |

FOREIGN PATENT DOCUMENTS

| EP | 0260716 | A1 | 9/1987 |
| EP | 0352375 | A1 | 7/1988 |
| EP | 1287812 | A2 | 6/2002 |
| EP | 1797865 | A2 | 6/2007 |
| WO | 2010072514 | A2 | 7/2010 |

OTHER PUBLICATIONS

"International Cosmetic Ingredient Dictionary and Handbook", (seventh edition 1997, The Cosmetic, Toiletry and Fragrance Association, 1101 17th Street, NW, Suite 300, Washington, DC 20036-4702).
International Search Report (PCT/EP2015/070358) dated Oct. 11, 2015.

\* cited by examiner

METHOD FOR THE SIMULTANEOUS PERMANENT SHAPING AND DYEING OF KERATINIC FIBERS

FIELD OF THE INVENTION

The present invention generally relates to a method for the permanent shaping and color modification of keratinic fibers, in particular human hair, in a single process.

BACKGROUND OF THE INVENTION

Permanent deformation of keratin-containing fibers is usually carried out in such a way that the fiber is mechanically deformed, and the deformation is fixed using suitable aids. Before and/or after this deformation, the fiber is treated with a keratin-reducing preparation. After a rinsing operation, the fiber is then treated with an oxidizing agent preparation in the so-called fixing step, rinsed, and the deformation aids (curlers, papillotes) are removed during or after the fixing step. When a mercaptan, for example ammonium thioglycolate, is used as the keratin-reducing component, the mercaptan cleaves a portion of the disulfide bridges of the keratin molecule to form thiol groups, resulting in softening of the keratin fiber or swelling of the fibers, with enlargement of the fiber diameter. During the subsequent oxidative fixing, disulfide bridges are re-linked in the keratin of the hair, so that the keratin structure is fixed in the specified deformation. Alternatively, it is known to use sulfite instead of the mercaptans for the hair deformation. By use of hydrogen sulfite solutions and/or sulfite solutions and/or disulfite solutions, disulfide bridges of the keratin are cleaved in a sulfitolysis process according to the equation

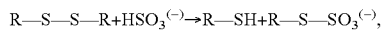
$$R\text{—}S\text{—}S\text{—}R + HSO_3^{(-)} \rightarrow R\text{—}SH + R\text{—}S\text{—}SO_3^{(-)},$$

thus achieving softening of the keratin fiber. Reducing agents including hydrogen sulfite, sulfite, or disulfite do not have the strong inherent odor of the mercaptan-containing agents. The cleavage, as described above, may be reversed in a fixing step, using an oxidizing agent, to form new disulfide bridges.

When dyeing of the keratinic fiber in addition to the shaping is also desired, the dyeing may be carried out as a separate treatment before or after the shaping that takes place. However, in particular in the case of oxidative dyeing, this results in extreme stress on the keratinic fibers, since each oxidative treatment of the fibers damages their internal structure. In addition, such an operation is very time-consuming, since a period of two weeks or more must be provided between the shaping and the dyeing treatment in order to avoid the above-described extreme stress and accompanying damage. For this reason, several methods for simultaneously shaping and dyeing keratinic fibers, in particular hair, have already been proposed. In many cases, for this purpose an oxidizing agent preparation that includes substantive dyes and/or oxidation dye precursors in addition to the oxidizing agent is used in the fixing step. Such a procedure is described in DE 19713698 C1, for example. However, this procedure has the disadvantage that the dyeing takes place at the same time as the fixing, i.e., at a time when the fibers to be treated are placed on deformation aids and are thus under mechanical tension. This hinders the uniform application of the dye, so that there is a risk of a nonuniform dyeing result.

Methods for simultaneously shaping and dyeing of hair are known from EP 0352375 A1 and EP 1287812 A2, in which a keratin-reducing preparation that already includes the necessary substantive dyes and/or oxidation dye precursors is used. At least a portion of the particular keratin-reducing preparation is applied to the hair after it has been mechanically deformed. However, the substantive dyes and/or oxidation dye precursors used for the dyeing do not always have satisfactory stability with respect to the keratin-reducing preparation, so that nonuniform shaping and dyeing results may occur in the event that the substantive dyes and/or oxidation dye precursors react with the keratin-reducing preparation.

It is therefore desirable to provide a method for shaping and dyeing keratinic fibers, in particular human hair, in which the shaping and the dyeing may be carried out in a single process, and which gives a comparable or better shaping result, uniformly dyes the keratinic fibers in the desired tint, and results in little or even no damage to the hair. Furthermore, other desirable features and characteristics of the present invention will become apparent from the subsequent detailed description of the invention and the appended claims, taken in conjunction with this background of the invention.

BRIEF SUMMARY OF THE INVENTION

A first subject matter of the invention therefore relates to a method for the permanent shaping and color modification of keratinic fibers, in particular human hair, in a single process, the method comprising the following method steps in the stated sequence. First, an aqueous composition (M1), including at least one keratin-reducing compound and at least one alkalizing agent, is applied to the keratinic fibers and leaving this composition (M1) on the keratinic fibers for a period of 5 to 50 minutes at a temperature of 20 to 45° C. The keratinic fibers are rinsed, and optionally dried using a towel and/or hair dryer. Next, a composition (M2), including at least one oxidation dye precursor and at least one oxidizing agent, is applied to the keratinic fibers and deforming the keratinic fibers, using deformation aids. The composition (M2) is allowed to act for 10 to 35 minutes. An aqueous composition (M3), including at least one oxidizing agent, is next applied to the keratinic fibers and is left on the keratinic fibers for 30 seconds to 15 minutes. The keratinic fibers are rinsed out, along with removal of the deformation aids. Optionally, an aftertreatment agent may then be applied to the keratinic fibers.

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

It has surprisingly been found that that the above-described objectives are achieved by a method in which, after applying a reducing agent composition and a dye composition using deformation aids, the keratinic fibers are deformed, and the deformation is subsequently fixed by a fixative. The method according to the invention results in an excellent shaping result as well as uniform and intensive dyeing or lightening. In addition, when the method procedure according to the invention is used, there is surprisingly little or no damage to the hair. Carrying out the shaping step and the dyeing step in succession allows significant time savings compared to the shaping and dyeing in two separate processes.

In principle, all animal hair, for example wool, horsehair, angora hair, fur, feathers, and products or textiles produced therefrom, may be used as keratin-containing fibers. However, the invention is preferably implemented within the scope of simultaneous hair shaping and dyeing, in particular permanent waving and dyeing of straight hair and wigs made therefrom.

According to the invention, the permanent deformation and color modification, i.e., the permanent wave and oxidative hair dyeing, is carried out in a single process. In this regard, "in a single process" means that there is a period of 30 seconds to 2 hours, preferably 30 seconds to 1 hour, more preferably 30 seconds to 30 minutes, in particular 30 seconds to 15 minutes, between the end of one method step and the beginning of the next method step.

Within the meaning of the method according to the invention, deformation aids are preferably so-called permanent wave curlers or papillotes.

Particularly preferred methods according to the invention result in waving of the keratinic fibers with simultaneous lightening or color modification of the hair color that is present before the method according to the invention is carried out. Therefore, a permanent wave is preferably carried out as permanent shaping, and lightening or dyeing is preferably carried out as color modification.

In the first method step (method step a)) of the method according to the invention, the keratinic fibers are deformed, using deformation aids. In this regard, in particular permanent wave curlers or papillotes are suited as deformation aids. To facilitate placing the keratinic fibers on the deformation aids, it may be preferable according to the invention for the keratin-containing fibers to be moistened with water or washed with a hair cleaning agent prior to method step a). Using a hair cleaning agent, in particular a hair shampoo, may be advantageous when the hair is very dirty. After rinsing out the hair shampoo, the hair is then rubbed with a towel so that perceptible residual moisture remains in the hair. If the hair is not very dirty, it is preferable to moisten the keratinic fibers with water to ensure separation into defined, individual strands of hair. This may take place, for example, by spraying the fibers with a liquid, preferably water.

The aqueous composition (M1) is left on the keratinic fibers for a period of 5 to 50 minutes in method step a). According to the invention, however, fairly short exposure times to the reducing agent are preferred. Particularly preferred methods according to the invention are therefore characterized in that the composition (M1) used in method step a) is left on the keratinic fibers for a period of 10 to 50 minutes, preferably 10 to 45 minutes, more preferably 10 to 40 minutes, in particular 20 to 40 minutes. Due to the use of a reducing agent (M1), a portion of the disulfide bridges of the keratin molecule is reduced to form thiol groups, resulting in softening of the keratin fibers. To obtain a uniform shaping result, in particular a permanent wave result, the reducing agent (M1) should be applied uniformly to the keratinic fibers. For this purpose, it may be preferable to repeat the application of the reducing agent several times.

Following the exposure time to the reducing agent, in a second method step (method step b)) the keratinic fibers are rinsed out with water and optionally rubbed with a towel and/or dried with a hair dryer. After completion of the rubbing step, perceptible residual moisture remains in the keratinic fibers; i.e., no dry keratinic fibers are present. Dry keratinic fibers preferably result when a hair dryer is used. "Dry keratinic fibers" is understood to mean fibers whose moisture content is substantially in equilibrium with the moisture in the air, or which absorb the moisture from the ambient air.

After rinsing the keratinic fibers, in method step c) of the method according to the invention a composition (M2), also referred to below as a coloring agent, is applied to the keratinic fibers, and after applying this composition the keratinic fibers are deformed, using deformation aids. To ensure uniform wetting of the keratinic fibers, it may be preferable to apply coloring agent to the keratinic fibers several times in succession. The oxidizing agent, in particular hydrogen peroxide, present in the coloring agent on the one hand results in partial oxidation of the thiol groups of the softened keratinic fibers, and thus, prefixing of the shaped, in particular waved, keratinic fibers. On the other hand, the oxidizing agent in the composition (M2) results in formation of the desired color from the oxidation dye precursors, in particular lightening or dyeing of the keratinic fibers.

To avoid excessive stress and damage to the keratinic fibers while carrying out the method according to the invention, deformation aids having a specific diameter are preferably used in method step c). Particularly preferred methods according to the invention are therefore characterized in that the deformation aids used in method step c) have a diameter of 1 to 10 cm, preferably 1 to 8 cm, more preferably 1 to 6 cm, in particular 2 to 5 cm.

The composition (M2) applied in method step c) is allowed to act for a period of 10 to 30 minutes (method step d)). According to the invention, however, fairly short exposure times to the coloring agent are preferred. Methods according to the invention are therefore characterized in that the composition (M2) used in method step d) is left on the keratinic fibers for a period of 20 to 35 minutes, preferably 20 to 30 minutes, in particular 20 to 25 minutes.

In order to sufficiently fix the keratinic fibers in the desired shape, in method step e) of the method according to the invention an aqueous composition (M3), also referred to below as fixative, is applied to the keratinic fibers and left on the fibers for a period of 30 seconds to 15 minutes. The complete oxidation of the thiol groups of the keratin of the hairs to form disulfide groups, and thus the complete fixing of the fibers in the desired shape, is ensured by using a fixative that likewise includes an oxidizing agent. It may be preferable to apply fixative to the keratinic fibers several times in succession to ensure uniform wetting of the keratinic fibers.

After the fixative (M3) is rinsed out, with removal of the deformation aids, in method step f) of the method according to the invention, shaping, in particular waving, as well as color modification, in particular lightening or dyeing, of the keratinic fibers is directly obtained without having to carry out a further oxidative dyeing operation, and without excessively damaging the keratinic fibers due to the simultaneous waving and lightening or dyeing. Considerable time savings may thus be achieved compared to carrying out the waving and lightening or dyeing as two separate processes, since there may typically be a certain period of 1 to 3 weeks between these processes in order to avoid damage to the hair. Within the scope of the method according to the invention, it is preferable to use water having a temperature of 20 to 45° C. for the rinsing of the keratinic fibers carried out in method step f).

The aqueous composition (M1) used in method step a) is a reducing agent that includes at least one keratin-reducing compound. According to the invention, an aqueous composition is understood to mean a composition that includes at least 50% by weight water, based on the total weight of the composition. This aqueous composition (M1) may be present in various forms, for example as a lotion, oil-in-water emulsion, or water-in-oil emulsion. According to the invention, the composition (M1) used as a keratin-reducing compound in method step (b) preferably includes at least one compound from the group comprising thioglycolic acid, thiolactic acid, thiomalic acid, phenylthioglycolic acid, mercaptoethanesulfonic acid, and the salts and esters thereof, cysteamine, cysteine, Bunte salts and salts of sulfurous acid, alkali disulfites, for example sodium disulfite ($Na_2S_2O_5$) and potassium disulfite ($K_2S_2O_5$), and magnesium disulfite and ammonium disulfite (($NH_4)_2S_2O_5$), hydrogen sulfites as alkali, magnesium, ammonium, or alkanolammonium salts based on a $C_2$-$C_4$ mono-, di-, or trialkanolamine, and sulfites as alkali, ammonium, or alkanolammonium salts based on a $C_2$-$C_4$ mono-, di-, or trialkanolamine. The above-mentioned compounds are able to reduce the disulfide bridges of the keratin to form thiol groups, and thus to ensure the softening of the keratin fibers necessary for the shaping.

Within the scope of this embodiment, it has proven to be particularly advantageous when the composition (M1) used as a keratin-reducing compound in method step a) includes at least one compound from the group comprising thioglycolic acid, thiolactic acid, and cysteine, and the salts thereof. Using the above-mentioned keratin-reducing compounds ensures a sufficient reduction of the disulfide bridges at relatively low use concentrations, so that the development of unpleasant odors during the shaping may be largely avoided.

According to the invention, the composition (M1) used in method step a) preferably includes the at least one keratin-reducing compound in an overall quantity of 5 to 20% by weight, preferably 7 to 18% by weight, more preferably 9 to 16% by weight, in particular 10 to 15% by weight, based on the total weight of the aqueous composition (M1). Using such quantities ensures sufficient softening of the keratin fibers, but without excessively damaging the fibers or releasing unpleasant odors during the application. A good shaping result without excessive damage to the hair may thus be achieved.

The reducing agents (M1) used in method step a) also include at least one alkalizing agent for setting the desired pH and for assisting with hair swelling, i.e., enlargement of the hair diameter. The composition (M1) used in method step a) preferably includes as alkalizing agent at least one compound from the group comprising sodium hydroxide, potassium hydroxide, ammonium hydroxide, ammonia, monoethanolamine, 2-amino-2-methylpropane, and alkali and ammonium hydrogen carbonates. These alkalizing agents are stable even in the presence of the reducing compound(s), and do not result in instability or pH fluctuations of the reducing agents (M1).

In this regard, it is advantageous when the composition (M1) used in method step a) includes ammonium hydrogen carbonate and/or ammonium hydroxide as alkalizing agent. Use of these alkalizing agents has proven to be particularly advantageous with regard to the pH stability and storage stability of the reducing agents (M1).

According to one embodiment of the present invention, the composition (M1) used in method step a) includes the at least one alkalizing agent in an overall quantity of 0.1 to 15% by weight, preferably 0.5 to 12% by weight, more preferably 1.0 to 10% by weight, in particular 1.5 to 7% by weight, based on the total weight of the aqueous composition (M1). Use of the above-mentioned quantities results in superior assistance in hair swelling. In addition, the setting of the desired pH values of pH 5 to pH 12 is ensured when these quantities are used.

Within the scope of the present invention, compositions (M1) preferably used in method step b) therefore have a pH of 5 to 12, preferably 5 to 10, in particular 5 to 9.5, at 20° C.

Particularly good results are obtained within the scope of the present invention when the composition (M1) used in method step a) has a weight ratio of the keratin-reducing compound to the alkalizing agent of 1:200 to 1:1, preferably 1:50 to 1:1, more preferably 1:30 to 1:1, very preferably 1:20 to 1:1, in particular 1:10 to 1:1. Use of the above-mentioned weight ratios results in particularly effective hair softening and hair swelling, and thus ensures a long-lasting shaping result that also is not significantly influenced by the subsequent dyeing step, in particular the lightening or dyeing step.

The aqueous composition (M1) may include further active substances and ingredients in addition to the above-mentioned ingredients. The composition (M1) used in method step a) preferably additionally includes at least one further compound selected from the group of (i) surfactants; (ii) cationic polymers; (iii) protein hydrolysates; (iv) oils; (v) thickeners; and (vi) the mixtures thereof.

Within the meaning of the present invention, surfactants are amphiphilic (bifunctional) compounds composed of at least one hydrophobic and at least one hydrophilic molecular portion. A basic property of surfactants and emulsifiers is the oriented absorption to boundary surfaces, and the aggregation into micelles and the formation of lyotrophic phases. Within the scope of the present invention, usable surfactants are selected from the group of nonionic surfactants, anionic surfactants, amphoteric surfactants, zwitterionic surfactants, cationic surfactants, and the mixtures thereof.

According to the invention, reducing agents (M1) are particularly preferably used in the method according to the invention which additionally include at least one nonionic surfactant from the group comprising (i) alkylene oxide addition products with alcohols having 8 to 30 carbon atoms or carboxylic acids having 8 to 30 carbon atoms, which include 2 to 30 moles of ethylene oxide per mole of alcohol or carboxylic acid, respectively; (ii) carboxylic acid esters of ethoxylated and/or propoxylated glycerin having 8 to 30 carbon atoms in the carboxylic acid chain and 1 to 30 moles of ethylene oxide and/or propylene oxide per mole of glycerin; (iii) alkyl polyglucosides of formula $R^1O$-$[G]_p$, where $R^1$ stands for an alkyl and/or alkenyl functional group including 4 to 22 carbon atoms, G stands for a sugar functional group including 5 or 6 carbon atoms, and p stands for numbers from 1 to 10; and (iv) the mixtures thereof.

Particularly preferred methods according to the invention are therefore characterized in that the aqueous composition (M1) additionally includes at least one nonionic surfactant from the group comprising alkyl polyglucosides of formula $R^1O$-$[G]_p$, where $R^1$ stands for an alkyl and/or alkenyl functional group including 4 to 22 carbon atoms, G stands for a sugar functional group including 5 or 6 carbon atoms, and p stands for numbers from 1 to 10, in an overall quantity of 0.1 to 10% by weight, preferably 0.5 to 5% by weight, in particular 0.8 to 3% by weight, based on the total weight of the composition (M1). In the formula $R^1O$-$[G]_p$, the index number p indicates the degree of oligeromerization (DP), i.e., the distribution of mono- and oligoglucosides, and stands for a number between 1 and 10. While p in a given compound must always be an integer, and may primarily assume the values p=1 through 6 here, the value p for a specific alkyl oligoglucoside is an analytically determined mathematical variable which usually represents a fractional number. Alkyl and/or alkenyl oligoglucosides having an average degree of oligeromerization p of 1.1 to 3.0 are preferably used according to the invention. From an application standpoint, alkyl and/or alkenyl oligoglucosides are preferred whose degree of oligeromerization is less than 1.7, in particular between 1.2 and 1.7. The alkyl or alkenyl functional group $R^1$ may be derived from primary alcohols including 4 to 20, preferably 8 to 16, carbon atoms. Very particularly preferred according to the invention are alkyl oligoglucosides based on hydrogenated $C_{12/14}$ coco alcohol having a DP of 1 to 3, as are commercially available, for example, under the INCI name "Coco Glucoside." For example, addition products of 20 to 60 moles of ethylene oxide with castor oil and hydrogenated castor oil, in particular the compounds known under the INCI names PEG-40 Hydrogenated Castor Oil and PEG-60 Hydrogenated Castor Oil, are also suitable nonionic surfactants.

Furthermore, the aqueous compositions (M1) may additionally include at least one anionic surfactant. Preferred anionic surfactants are fatty acids, alkyl sulfates, alkyl ether sulfates, and ethercarboxylic acids including 10 to 20 carbon atoms in the alkyl group and up to 16 glycol ether groups in the molecule. The anionic surfactants are used in an overall quantity of 0.1 to 45% by weight, preferably 1 to 30% by weight, in particular 1 to 15% by weight, based on the total weight of the composition (M1).

In addition, it is likewise possible for the reducing agents (M1) to additionally include at least one zwitterionic and/or amphoteric surfactant. Preferred zwitterionic surfactants are betaines, N-alkyl-N,N-dimethylammonium glycinates, N-acylaminopropyl-N,N-dimethylammonium glycinates, and 2-alkyl-3-carboxymethyl-3-hydroxyethyl imidazolines. A particularly preferred zwitterionic surfactant is known under the INCI name Cocamidopropyl Betaine. Preferred amphoteric surfactants are N-alkylglycines, N-alkylpropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids, and alkylaminoacetic acids. Particularly preferred amphoteric surfactants are N-cocoalkylamino propionate, cocoacylaminoethylamino propionate, and $C_{12}$-$C_{18}$ acyl sarcosine. The zwitterionic and/or amphoteric surfactants are used in an overall quantity of 0.1 to 45% by weight, preferably 1 to 30% by weight, in particular 1 to 15% by weight, based on the total weight of the composition (M1).

The composition (M1) may also include at least one cationic polymer. Cationic polymers are understood to mean polymers that have groups in the main chain and/or side chain which may be "temporarily" or "permanently" cationic. According to the invention, "permanently cationic" polymers refer to those polymers which have a cationic group, regardless of the pH of the agent. These are generally polymers that include a quaternary nitrogen atom, for example in the form of an ammonium group. Quaternary ammonium groups are preferred cationic groups. In particular, those polymers in which the quaternary ammonium group is bound via a $C_{1-4}$ hydrocarbon group to a polymer main chain composed of acrylic acid, methacrylic acid, or the derivatives thereof have proven to be particularly suitable.

Particularly preferred cationic polymers are selected from the compounds with the INCI name "Polyquaternium." Polyquaternium-2, Polyquaternium-4, Polyquaternium-5, Polyquaternium-6, Polyquaternium-7, Polyquaternium-10, Polyquaternium-11, Polyquaternium-17, Polyquaternium-18, Polyquaternium-22, Polyquaternium-27, Polyquaternium-37, and Polyquaternium-39 are particularly preferably used; Polyquaternium-22, Polyquaternium-37, and Polyquaternium-39 are extremely preferred, and Polyquaternium-22 is most preferred.

The following are examples of additional preferred cationic polymers:
  quaternized cellulose derivatives, as are commercially available under the names Celquat® and Polymer JR®. The compounds Celquat® H 100, Celquat® L 200, and Polymer JR® 400 are preferred quaternized cellulose derivatives,
  cationized honey, for example the commercial product Honeyquat® 50,
  cationic guar derivatives, such as in particular the products marketed under the trade names Cosmedia® Guar and Jaguar®,
  polysiloxanes having quaternary groups, for example the commercially available products Q2-7224 (manufacturer: Dow Corning; a stabilized trimethylsilylamodimethicone), Dow Corning® 929 Emulsion (containing a hydroxylamino-modified silicone, also referred to as amodimethicone), SM-2059 (manufacturer: General Electric), SLM-55067 (manufacturer: Wacker), and Abil®-Quat 3270 and 3272 (manufacturer: Th. Goldschmidt; diquaternary polydimethylsiloxanes, Quaternium-80),
  polymeric dimethyldiallyl ammonium salts and the copolymers thereof with esters and amides of acrylic acid and methacrylic acid. The products commercially available under the names Merquat®100 (poly(dimethyldiallyl ammonium chloride)) and Merquat® 550 (dimethyldiallyl ammonium chloride-acrylamide copolymer) are examples of such cationic polymers,
  copolymers of vinylpyrrolidone with quaternized derivatives of dialkylaminoalkyl acrylate and methacrylate, such as vinylpyrrolidone-dimethylaminoethyl methacrylate copolymers quaternized with diethyl sulfate, for example. Such compounds are commercially available under the names Gafquat® 734 and Gafquat® 755,
  vinylpyrrolidone-vinylimidazolium methochloride copolymers, as marketed under the names Luviquat® FC 370, FC 550, FC 905, and HM 552,
  quaternized polyvinyl alcohol.

Likewise usable according to the invention are the copolymers of vinylpyrrolidone, such as those available as the commercial products Copolymer 845 (manufacturer: ISP), Gaffix® VC 713 (manufacturer: ISP), Gafquat® ASCP 1011, Gafquat® HS 110, Luviquat® 8155, and Luviquat® MS 370.

The cationic polymers are included in the composition (M1) in an overall quantity of 0.1 to 5.0% by weight, in particular 0.25 to 3.0% by weight, based on the total weight of the composition (M1).

In another embodiment of the invention, the aqueous compositions (M1) may also include protein hydrolysates and/or the derivatives thereof. Protein hydrolysates are product mixtures obtained by acidic, basic, or enzymatically catalyzed degradation of proteins. Protein hydrolysates of plant and animal origin may be used according to the invention.

Cationized protein hydrolysates are usable according to the invention, wherein the underlying protein hydrolysate may originate from animals, for example from collagen, milk, or keratin, from plants, for example from wheat, corn, rice, potatoes, soybeans, or almonds, from marine life forms, for example from fish collagen or algae, or from biotechnology-derived protein hydrolysates. The protein hydrolysates on which the cationic derivatives according to the invention are based may be obtained from the corresponding proteins by chemical, in particular alkaline or acidic, hydrolysis, by enzymatic hydrolysis, and/or by a combination of the two types of hydrolysis. The hydrolysis of proteins generally results in a protein hydrolysate having a molecular weight distribution of approximately 100 Dalton all the way to several thousand Dalton. Cationic protein hydrolysates whose underlying protein component has a molecular weight of 100 to 25,000 Dalton, preferably 250 to 5000 Dalton, are preferred.

Quaternized amino acids and the mixtures thereof are also understood to be cationic protein hydrolysates. The quaternization of the protein hydrolysates or the amino acids is often carried out using quaternary ammonium salts, for example N,N-dimethyl-N-(n-alkyl)-N-(2-hydroxy-3-chloron-propyl)ammonium halides. In addition, the cationic protein hydrolysates may be even further derivatized. Typical examples of the cationic protein hydrolysates and derivatives according to the invention are the commercially available products listed under the INCI names in the International Cosmetic Ingredient Dictionary and Handbook, (Seventh Edition 1997, The Cosmetic, Toiletry, And Fragrance Association, 1101 17th Street, N.W., Suite 300, Washington, D.C. 20036-4702): Cocodimonium Hydroxypropyl Hydrolyzed Collagen, Cocodimonium Hydroxypropyl Hydrolyzed Casein, Cocodimonium Hydroxypropyl Hydrolyzed Hair Keratin, Cocodimonium Hydroxypropyl Hydrolyzed Keratin, Cocodimonium Hydroxypropyl Hydrolyzed Rice Protein, Cocodimonium Hydroxypropyl Hydrolyzed Silk, Cocodimonium Hydroxypropyl Hydrolyzed Soy Protein, Cocodimonium Hydroxypropyl Hydrolyzed Wheat Protein, Cocodimonium Hydroxypropyl Silk Amino Acids, Hydroxypropyl Arginine Lauryl/Myristyl Ether HCl, Hydroxypropyltrimonium Gelatin, Hydroxypropyltrimonium Hydrolyzed Casein, Hydroxypropyltrimonium Hydrolyzed Collagen, Hydroxypropyltrimonium Hydrolyzed Conchiolin Protein, Hydroxypropyltrimonium Hydrolyzed Keratin, Hydroxypropyltrimonium Hydrolyzed Rice Bran Protein, Hydroxyproypltrimonium Hydrolyzed Silk, Hydroxypropyltrimonium Hydrolyzed Soy Protein, Hydroxypropyl Hydrolyzed Vegetable Protein, Hydroxypropyltrimonium Hydrolyzed Wheat Protein, Hydroxypropyltrimonium Hydrolyzed Wheat Protein/Siloxy Silicate, Laurdimonium Hydroxypropyl Hydrolyzed Soy Protein, Laurdimonium Hydroxypropyl Hydrolyzed Wheat Protein, Laurdimonium Hydroxypropyl Hydrolyzed Wheat Protein/Siloxy Silicate, Lauryldimonium Hydroxypropyl Hydrolyzed Casein, Lauryldimonium Hydroxypropyl Hydrolyzed Collagen, Lauryldimonium Hydroxypropyl Hydrolyzed Keratin, Lauryldimonium Hydroxypropyl Hydrolyzed Silk, Lauryldimonium Hydroxypropyl Hydrolyzed Soy Protein, Steardimonium Hydroxypropyl Hydrolyzed Casein, Steardimonium Hydroxypropyl Hydrolyzed Collagen, Steardimonium Hydroxypropyl Hydrolyzed Keratin, Steardimonium Hydroxypropyl Hydrolyzed Rice Protein, Steardimonium Hydroxypropyl Hydrolyzed Silk, Steardimonium Hydroxypropyl Hydrolyzed Soy Protein, Steardimonium Hydroxypropyl Hydrolyzed Vegetable Protein, Steardimonium Hydroxypropyl Hydrolyzed Wheat Protein, Steartrimonium Hydroxyethyl Hydrolyzed Collagen, Quaternium-76 Hydrolyzed Collagen, Quaternium-79 Hydrolyzed Collagen, Quaternium-79 Hydrolyzed Keratin, Quaternium-79 Hydrolyzed Milk Protein, Quaternium-79 Hydrolyzed Silk, Quaternium-79 Hydrolyzed Soy Protein, and Quaternium-79 Hydrolyzed Wheat Protein. The plant-based cationic protein hydrolysates and derivatives are particularly preferred.

The protein hydrolysates and the derivatives thereof are preferably used in an overall quantity of 0.01 to 10% by weight, based on the total weight of the composition (M1). An overall quantity of 0.1 to 5% by weight, preferably 0.1 to 3% by weight, based on the total weight of the composition (M1), is very particularly preferred.

Within the scope of the present invention, it may also be preferable for the reducing agents (M1) to include at least one oil selected from the group comprising sunflower oil, corn oil, soybean oil, pumpkin seed oil, grape seed oil, sesame oil, hazelnut oil, apricot kernel oil, orange oil, macadamia nut oil, arara oil, castor oil, avocado oil, and the mixtures thereof in an overall quantity of 0.1 to 10% by weight, preferably 0.2 to 5.0% by weight, in particular 0.5 to 2.0% by weight, based on the total weight of the cosmetic agent (M1).

The reducing agents (M1) particularly preferably include orange oil in an overall quantity of 0.001 to 1.0% by weight, preferably 0.005 to 0.5% by weight, in particular 0.01 to 0.1% by weight, based on the total weight of the composition (M1).

Thickeners may be used for thickening the aqueous composition (M1). Within the scope of the present invention, for example substances selected from cellulose ethers, xanthan gum, sclerotium gum, succinoglucans, polygalactomannans, pectins, agar, carrageenan, tragacanth, gum arabic, karaya gum, tara gum, gellan, gelatin, propylene glycol alginate, alginic acids and the salts thereof, polyvinylpyrrolidones, polyvinyl alcohols, polyacrylamides, starches that are physically modified (by pregelatinization, for example) and/or chemically modified, acrylic acid-acrylate copolymers, acrylic acid-acrylamide copolymers, acrylic acid-vinylpyrrolidone copolymers, acrylic acid-vinyl formamide copolymers, polyacrylates, and crosslinked polymers of acrylic acid or methacrylic acid and the salts thereof are suitable as thickeners. Particularly preferred thickeners are selected from cellulose ethers, in particular hydroxyalkyl celluloses.

The thickener is preferably used in the composition (M1) in an overall quantity of 0.05 to 2% by weight, in particular 0.1 to 1% by weight, based on the total weight of the composition (M1).

The composition (M2) used in method step c) is an oxidative hair dye, in particular a coloring agent, which lightens or modifies the hair color that is present prior to carrying out the method according to the invention. According to the invention, the composition (M2) used in method step d) therefore preferably includes at least one oxidation dye precursor in the form of a developer component and at least one oxidation dye precursor in the form of a coupler component. Particularly good dyeing results are obtained when oxidation dye precursors of the developer type and of the coupler type are used in the coloring agents (M2).

The developer components and coupler components are generally used in the free form. However, for substances including amino groups, it may be preferable to use their salt form, in particular in the form of the hydrochlorides and hydrobromides or the sulfates.

According to the invention, compositions (M2) are preferred which include the developer components and coupler components in each case in an overall quantity of 0.001 to 10% by weight, preferably 0.01 to 8% by weight, more preferably 0.1 to 5% by weight, in particular 0.5 to 3% by weight, based on the total weight of the composition (M2).

In another preferred embodiment, the method according to the invention is therefore characterized in that the composition (M2) used in method step c) includes the at least one oxidation dye precursor in an overall quantity of 0.001 to 10% by weight, preferably 0.01 to 8% by weight, more preferably 0.1 to 5% by weight, in particular 0.5 to 3% by weight, based on the total weight of the composition (M2).

Suitable oxidation dye precursors of the developer type are, for example, p-phenylenediamine and the derivatives thereof. Preferred p-phenylenediamines are selected from one or more compounds of the group comprising p-phenylenediamine, p-toluylenediamine, 2-chloro-p-phenylenediamine, 2,3-dimethyl-p-phenylenediamine, 2,6-dimethyl-p-phenylenediamine, N,N-bis-(2-hydroxyethyl)-p-phenylenediamine, 2-(2-hydroxyethyl)-p-phenylenediamine, 2-(1,2-dihydroxyethyl)-p-phenylenediamine, N-(2-hydroxypropyl)-p-phenylenediamine, N-(4'-aminophenyl)-p-phenylenediamine, 2-methoxymethyl-p-phenylenediamine, N-phenyl-p-phenylenediamine, 2-(2-hydroxyethyloxy)-p-phenylenediamine, and N-(4-amino-3-methyl-phenyl)-N-[3-(1H-imidazol-1-yl)propyl]amine, and the physiologically acceptable salts thereof.

It may also be preferable according to the invention to use, as the developer component, compounds that include at least two aromatic nuclei that are substituted with amino and/or hydroxyl groups. Preferred binuclear developer components are selected from N,N'-bis-(2-hydroxyethyl)-N,N'-bis-(4'-aminophenyl)-1,3-diaminopropan-2-ol, N,N'-bis-(4-aminophenyl)-1,4-diazacycloheptane, bis-(2-hydroxy-5-aminophenyl)methane, and the physiologically acceptable salts thereof.

Furthermore, it may be preferable according to the invention to use a p-aminophenol derivative or one of the physiologically acceptable salts thereof as the developer component. Preferred p-aminophenols are p-aminophenol, N-methyl-p-aminophenol, 4-amino-3-methylphenol, 4-amino-2-aminomethylphenol, 4-amino-2-(1,2-dihydroxyethyl)phenol, 4-amino-2-(diethylaminomethyl)phenol, and the physiologically acceptable salts thereof.

Moreover, the developer component may be selected from o-aminophenol and the derivatives thereof, preferably 2-amino-4-methylphenol, 2-amino-5-methylphenol, 2-amino-4-chlorophenol, and/or the physiologically acceptable salts thereof.

In addition, the developer component may be selected from heterocyclic developer components such as pyrimidine derivatives, pyrazole derivatives, pyrazolopyrimidine derivatives, and the physiologically acceptable salts thereof. Preferred pyrimidine derivatives are 2,4,5,6-tetraaminopyrimidine, 4-hydroxy-2,5,6-triaminopyrimidine, and the physiologically acceptable salts thereof. A preferred pyrazole derivative is 4,5-diamino-1-(2-hydroxyethyl)pyrazole and the physiologically acceptable salts thereof. Pyrazolo[1,5-a]pyrimidines in particular are preferred as pyrazolopyrimidines.

Preferred oxidation dye precursors of the developer type are therefore selected from the group comprising p-phenylenediamine, p-toluylenediamine, 2-(2-hydroxyethyl)-p-phenylenediamine, 2-(1,2-dihydroxyethyl)-p-phenylenediamine, N,N'-bis-(2-hydroxyethyl)-p-phenylenediamine, 2-methoxymethyl-p-phenylenediamine, N-(4-amino-3-methylphenyl)-N-[3-(1H-imidazol-1-yl)propyl]amine, N,N'-bis-(2-hydroxyethyl)-N,N'-bis-(4-aminophenyl)-1,3-diaminopropan-2-ol, bis-(2-hydroxy-5-aminophenyl)methane, 1,3-bis-(2,5-diaminophenoxy)propan-2-ol, N,N'-bis-(4-aminophenyl)-1,4-diazacycloheptane, 1,10-bis-(2,5-diaminophenyl)-1,4,7,10-tetraoxadecane, p-aminophenol, 4-amino-3-methylphenol, 4-amino-2-aminomethylphenol, 4-amino-2-(1,2-dihydroxyethyl)phenol and 4-amino-2-(diethylaminomethyl)phenol, 4,5-diamino-1-(2-hydroxyethyl)pyrazole, 2,4,5,6-tetraaminopyrimidine, 4-hydroxy-2,5,6-triaminopyrimidine, 2-hydroxy-4,5,6-triaminopyrimidine, or the physiologically acceptable salts of these compounds.

Particularly preferred developer components are p-toluylenediamine, 2-(2-hydroxyethyl)-p-phenylenediamine, 2-methoxymethyl-p-phenylenediamine, N-(4-amino-3-methylphenyl)-N-[3-(1H-imidazol-1-yl)propyl]amine, and/or 4,5-diamino-1-(2-hydroxyethyl)pyrazole, and the physiologically acceptable salts thereof.

The composition (M2) used in method step d), in addition to the at least one developer component, also includes at least one coupler component as oxidation dye precursor. m-Phenylenediamine derivatives, naphthols, resorcinol and resorcinol derivatives, pyrazolones, and m-aminophenol derivatives are generally used as coupler components.

Coupler components preferred according to the invention are selected from
 a) m-aminophenol and the derivatives thereof, in particular 3-aminophenol, 5-amino-2-methylphenol, 3-amino-2-chloro-6-methylphenol, 5-amino-4-chloro-2-methylphenol, 5-(2'-hydroxyethyl)-amino-2-methylphenol, and 2,4-dichloro-3-aminophenol,
 b) o-aminophenol and the derivatives thereof, such as 2-amino-5-ethylphenol,
 c) m-diaminobenzene and the derivatives thereof, for example 2,4-diaminophenoxyethanol, 1,3-bis-(2',4'-diaminophenoxy)propane, 1-methoxy-2-amino-4-(2'-hydroxyethylamino)benzene, 2,6-bis-(2'-hydroxyethylamino)-1-methylbenzene, 2-({3-[(2-hydroxyethyl)amino]-4-methoxy-5-methylphenyl}amino)ethanol, and 2-({3-[(2-hydroxyethyl)amino]-2-methoxy-5-methylphenyl}amino)ethanol,
 d) o-diaminobenzene and the derivatives thereof,
 e) di- or trihydroxybenzene derivatives, in particular resorcinol, 2-chlororesorcinol, 4-chlororesorcinol, 2-methylresorcinol, and 1,2,4-trihydroxybenzene,
 f) Pyridine derivatives, in particular 3-amino-2-methylamino-6-methoxypyridine, 2,6-diaminopyridine, 2,6-dihydroxy-3,4-dimethylpyridine, 2-amino-3-hydroxypyridine, and 3,5-diamino-2,6-dimethoxypyridine,
 g) naphthalene derivatives, such as 1-naphthol and 2-methyl-1-naphthol,
 h) morpholine derivatives, such as 6-hydroxybenzomorpholine,
 i) quinoxaline derivatives,
 j) pyrazole derivatives, such as 1-phenyl-3-methylpyrazol-5-one,
 k) indole derivatives, such as 6-hydroxyindole,
 l) pyrimidine derivatives, or
 m) methylenedioxybenzene derivatives, such as 1-(2'-hydroxyethyl)amino-3,4-methylenedioxybenzene and the physiologically acceptable salts thereof.

Coupler components preferred according to the invention are therefore selected from the group comprising 3-aminophenol, 5-amino-2-methylphenol, 3-amino-2-chloro-6-methylphenol, 2-hydroxy-4-aminophenoxyethanol, 5-amino-4-chloro-2-methylphenol, 5-(2-hydroxyethyl)amino-2-methylphenol, 2,4-dichloro-3-aminophenol, 2-aminophenol, 3-phenylenediamine, 2-(2,4-diaminophenoxy)ethanol, 1,3-bis(2,4-diaminophenoxy)propane, 1-methoxy-2-amino-4-(2-hydroxyethylamino)benzene, 1,3-bis(2,4-diaminophenyl)propane, 2,6-bis(2'-hydroxyethylamino)-1-methylbenzene, 2-({3-[(2-hydroxyethyl)amino]-

4-methoxy-5-methylphenyl}amino)ethanol, 2-({3-[(2-hydroxyethyl)amino]-2-methoxy-5-methylphenyl}amino) ethanol, 2-({3-[(2-hydroxyethyl)amino]-4,5-dimethylphenyl}amino)ethanol, 2-[3-morpholin-4-ylphenyl)amino]ethanol, 3-amino-4-(2-methoxyethoxy)-5-methylphenylamine, 1-amino-3-bis-(2-hydroxyethyl)aminobenzene, resorcinol, 2-methylresorcinol, 4-chlororesorcinol, 1,2,4-trihydroxybenzene, 2-amino-3-hydroxypyridine, 3-amino-2-methylamino-6-methoxypyridine, 2,6-dihydroxy-3,4-dimethylpyridine, 3,5-diamino-2,6-dimethoxypyridine, 1-phenyl-3-methylpyrazol-5-one, 1-naphthol, 1,5-dihydroxynaphthalene, 2,7-dihydroxynaphthalene, 1,7-dihydroxynaphthalene, 1,8-dihydroxynaphthalene, 4-hydroxyindole, 6-hydroxyindole, 7-hydroxyindole, 4-hydroxyindoline, 6-hydroxyindoline, 7-hydroxyindoline, or the physiologically acceptable salts of the above-mentioned compounds.

Coupler components particularly preferred according to the invention are resorcinol, 2-methylresorcinol, 5-amino-2-methylphenol, 3-aminophenol, 2-(2,4-diaminophenoxy) ethanol, 1,3-bis-(2,4-diamino-phenoxy)propane, 1-methoxy-2-amino-4-(2'-hydroxyethylamino)benzene, 2-amino-3-hydroxypyridine, 2,6-dihydroxy-3,4-dimethylpyridine, 1,5-dihydroxynaphthalene, 2,7-dihydroxynaphthalene, and 1-naphthol, and the physiologically acceptable salts thereof.

In another embodiment, the method according to the invention is characterized in that the composition (M2) used in method step d) includes as oxidation dye precursor at least one developer component and coupler component from the group comprising p-phenylenediamine, p-toluylenediamine, 2-(2-hydroxyethyl)-p-phenylenediamine, 2-(1,2-dihydroxyethyl)-p-phenylenediamine, N,N'-bis-(2-hydroxyethyl)-p-phenylenediamine, 2-methoxymethyl-p-phenylenediamine, N-(4-amino-3-methylphenyl)-N-[3-(1H-imidazol-1-yl)propyl]amine, N,N'-bis-(2-hydroxyethyl)-N,N'-bis-(4-aminophenyl)-1,3-diaminopropan-2-ol, bis-(2-hydroxy-5-aminophenyl)methane, 1,3-bis-(2, 5-diaminophenoxy)propan-2-ol, N,N'-bis-(4-aminophenyl)-1,4-diazacycloheptane, 1,10-bis-(2,5-diaminophenyl)-1,4,7,10-tetraoxadecane, p-aminophenol, 4-amino-3-methylphenol, 4-amino-2-aminomethylphenol, 4-amino-2-(1,2-dihydroxyethyl)phenol and 4-amino-2-(diethylaminomethyl)phenol, 4,5-diamino-1-(2-hydroxyethyl)pyrazole, 2,4,5,6-tetraaminopyrimidine, 4-hydroxy-2,5,6-triaminopyrimidine, 2-hydroxy-4,5,6-triaminopyrimidine, or the physiologically acceptable salts of these compounds, and additionally includes at least one coupler component from the group comprising 3-aminophenol, 5-amino-2-methylphenol, 3-amino-2-chloro-6-methylphenol, 2-hydroxy-4-aminophenoxyethanol, 5-amino-4-chloro-2-methylphenol, 5-(2-hydroxyethyl)-amino-2-methylphenol, 2,4-dichloro-3-aminophenol, 2-aminophenol, 3-phenylenediamine, 2-(2,4-diaminophenoxy)ethanol, 1,3-bis(2,4-diaminophenoxy)propane, 1-methoxy-2-amino-4-(2-hydroxyethylamino)benzene, 1,3-bis(2,4-diaminophenyl)propane, 2,6-bis(2'-hydroxyethylamino)-1-methylbenzene, 2-({3-[(2-hydroxyethyl)amino]-4-methoxy-5-methylphenyl}amino)ethanol, 2-({3-[(2-hydroxyethyl)amino]-2-methoxy-5-methyl-phenyl}amino)ethanol, 2-({3-[(2-hydroxyethyl)amino]-4, 5-dimethylphenyl}amino) ethanol, 2-[3-morpholin-4-ylphenyl)amino]ethanol, 3-amino-4-(2-methoxyethoxy)-5-methylphenylamine, 1-amino-3-bis-(2-hydroxyethyl)aminobenzene, resorcinol, 2-methylresorcinol, 4-chlororesorcinol, 1,2,4-trihydroxybenzene, 2-amino-3-hydroxypyridine, 3-amino-2-methylamino-6-methoxypyridine, 2,6-dihydroxy-3,4-dimethylpyridine, 3,5-diamino-2,6-dimethoxypyridine, 1-phenyl-3-methylpyrazol-5-one, 1-naphthol, 1,5-dihydroxynaphthalene, 2,7-dihydroxynaphthalene, 1,7-dihydroxynaphthalene, 1,8-dihydroxynaphthalene, 4-hydroxyindole, 6-hydroxyindole, 7-hydroxyindole, 4-hydroxyindoline, 6-hydroxyindoline, 7-hydroxyindoline, or the physiologically acceptable salts of the above-mentioned compounds.

Oxidation dye precursors of the developer type and of the coupler type are preferably used in specific combinations. Within the scope of the present invention, the following combinations have proven to be particularly advantageous: p-toluylenediamine/resorcinol; p-toluylenediamine/2-methylresorcinol; p-toluylenediamine/5-amino-2-methylphenol; p-toluylenediamine/3-aminophenol; p-toluylenediamine/2-(2,4-diaminophenoxy)ethanol; p-toluylenediamine/1,3-bis(2,4-diaminophenoxy)propane; p-toluylenediamine/1-methoxy-2-amino-4-(2-hydroxyethylamino)benzene; p-toluylenediamine/2-amino-3-hydroxypyridine; p-toluylenediamine/1-naphthol; 2-(2-hydroxyethyl)-p-phenylenediamine/resorcinol; 2-(2-hydroxyethyl)-p-phenylenediamine/2-methylresorcinol; 2-(2-hydroxyethyl)-p-phenylenediamine/5-amino-2-methylphenol; 2-(2-hydroxyethyl)-p-phenylenediamine/3-aminophenol; 2-(2-hydroxyethyl)-p-phenylenediamine/2-(2,4-diaminophenoxy)ethanol; 2-(2-hydroxyethyl)-p-phenylenediamine/1,3-bis-(2,4-diaminophenoxy)propane; 2-(2-hydroxyethyl)-p-phenylenediamine/1-methoxy-2-amino-4-(2-hydroxyethylamino)benzene; 2-(2-hydroxyethyl)-p-phenylenediamine/2-amino-3-hydroxypyridine; 2-(2-hydroxyethyl)-p-phenylenediamine/1-naphthol; 2-methoxymethyl-p-phenylenediamine/resorcinol; 2-methoxymethyl-p-phenylenediamine/2-methylresorcinol; 2-methoxymethyl-p-phenylenediamine/5-amino-2-methylphenol; 2-methoxymethyl-p-phenylenediamine/3-aminophenol; 2-methoxymethyl-p-phenylenediamine/2-(2, 4-diaminophenoxy)ethanol; 2-methoxymethyl-p-phenylenediamine/1,3-bis(2,4-diaminophenoxy)propane; 2-methoxymethyl-p-phenylenediamine/1-methoxy-2-amino-4-(2-hydroxyethylamino)benzene; 2-methoxymethyl-p-phenylenediamine/2-amino-3-hydroxypyridine; 2-methoxymethyl-p-phenylenediamine/1-naphthol; N-(4-amino-3-methylphenyl)-N-[3-(1H-imidazol-1-yl)propyl]amine/resorcinol; N-(4-amino-3-methylphenyl)-N-[3-(1H-imidazol-1-yl)propyl]amine/2-methylresorcinol; N-(4-amino-3-methylphenyl)-N-[3-(1H-imidazol-1-yl)propyl]amine/5-amino-2-methylphenol; N-(4-amino-3-methylphenyl)-N-[3-(1H-imidazol-1-yl)propyl]amine/3-aminophenol; N-(4-amino-3-methylphenyl)-N-[3-(1H-imidazol-1-yl)propyl]amine/2-(2, 4-diaminophenoxy) ethanol; N-(4-amino-3-methylphenyl)-N-[3-(1H-imidazol-1-yl)propyl]amine/1,3-bis(2,4-diaminophenoxy)propane; N-(4-amino-3-methylphenyl)-N-[3-(1H-imidazol-1-yl)propyl]amine/1-methoxy-2-amino-4-(2-hydroxyethylamino) benzene; N-(4-amino-3-methylphenyl)-N-[3-(1H-imidazol-1-yl)propyl]amine/2-amino-3-hydroxypyridine; N-(4-amino-3-methylphenyl)-N-[3-(1H-imidazol-1-yl)propyl]amine/1-naphthol; 4,5-diamino-1-(2-hydroxyethyl) pyrazole/resorcinol; 4,5-diamino-1-(2-hydroxyethyl) pyrazole/2-methylresorcinol; 4,5-diamino-1-(2-hydroxyethyl)pyrazole/5-amino-2-methylphenol; 4,5-diamino-1-(2-hydroxyethyl)pyrazole/3-aminophenol; 4, 5-diamino-1-(2-hydroxyethyl)pyrazole/2-(2, 4-diaminophenoxy)ethanol; 4,5-diamino-1-(2-hydroxyethyl)pyrazole/1,3-bis(2,4-diaminophenoxy)propane; 4,5-diamino-1-(2-hydroxyethyl)pyrazole/1-methoxy-2-amino-4-(2-hydroxyethylamino)benzene; 4,5-diamino-1-(2-hydroxyethyl)pyrazole/2-amino-3-hydroxypyridine; 4,5- diamino-1-(2-hydroxyethyl)pyrazole/1-naphthol. However, within the scope of the present invention it is also possible, in addition to the above-mentioned combinations, to additionally use further oxidation dye precursors in the composition (M2) used according to method step c).

Particularly attractive colorings are obtained when the composition (M2) used in method step c) includes at least one developer component selected from the group comprising p-phenylenediamine, p-toluylenediamine, N,N'-bis-(2-hydroxyethyl)amino-p-phenylenediamine, 1,3-bis-[(2-hydroxyethyl-4'-aminophenyl)amino]propan-2-ol, 1,10-bis-(2',5'-diaminophenyl)-1,4,7,10-tetraoxadecane, 4-aminophenol, 4-amino-3-methylphenol, bis-(5-amino-2-hydroxyphenyl)methane, 2,4,5,6-tetraaminopyrimidine, 2-hydroxy-4,5,6-triaminopyrimidine, 4,5-diamino-1-(2-hydroxyethyl)pyrazole, and the physiologically acceptable salts thereof and the mixtures thereof, and at least one coupler component selected from the group comprising resorcinol, 2-methylresorcinol, 5-methylresorcinol, 2,5-dimethylresorcinol, 4-chlororesorcinol, resorcinol monomethyl ether, 5-aminophenol, 5-amino-2-methylphenol, 5-(2-hydroxyethyl)amino-2-methylphenol, 3-amino-4-chloro-2-methylphenol, 3-amino-4-chloro-6-methylphenol, 3-amino-2,4-dichlorophenol, 2,4-diaminophenoxyethanol, 2-amino-4-(2'-hydroxyethyl)aminoanisol sulfate, 1,3-bis-(2,4-diaminophenoxy)propane, 2-amino-3-hydroxypyridine, 2-methylamino-3-amino-6-methoxypyridine, 2,6-dihydroxy-3,4-dimethylpyridine, 3,5-diamino-2,6-dimethoxypyridine, 1-naphthol, 2-methyl-1-naphthol, 1,5-dihydroxynaphthalene, 2,7-dihydroxynaphthalene, 1-phenyl-3-methylpyrazol-5-one, 2,6-bis-[(2'-hydroxyethyl)amino] toluene, 4-hydroxyindole, 6-hydroxyindole, 6-hydroxybenzomorpholine, and the physiologically acceptable salts thereof and the mixtures thereof.

Furthermore, in this regard it is preferred for the composition (M2) used in method step c) to include at least one developer component selected from p-toluylenediamine and the physiologically acceptable salts thereof, and at least one coupler component selected from the group comprising resorcinol, 2-methylresorcinol, 2-amino-3-hydroxypyridine, 3-aminophenol, and the physiologically acceptable salts thereof and the mixtures thereof. When the above-mentioned oxidation dye precursors are used, particularly good lightening or dyeing is achieved which has a high level of resistance against environmental influences such as hair washing, UV light, perspiration, and abrasion.

To obtain balanced and subtle shade formation, within the scope of the present invention it may also be provided that the composition (M2) used in method step c) additionally includes at least one substantive dye. Substantive dyes are dyes that are directly absorbed onto the hair, and require no oxidative process to form the color. Substantive dyes are usually nitrophenylenediamines, nitroaminophenols, azo dyes, anthraquinones, or indophenols.

Substantive dyes may be subdivided into anionic, cationic, and nonionic substantive dyes.

Preferred anionic substantive dyes are the compounds known under the names Acid Yellow 1, Yellow 10, Acid Yellow 23, Acid Yellow 36, Acid Orange 7, Acid Red 33, Acid Red 52, Pigment Red 57:1, Acid Blue 7, Acid Green 50, Acid Violet 43, Acid Black 1, Acid Black 52, and Tetrabromophenol Blue. Preferred cationic substantive dyes are cationic triphenylmethane dyes such as Basic Blue 7, Basic Blue 26, Basic Violet 2, and Basic Violet 14, aromatic systems substituted with a quaternary nitrogen group, such as Basic Yellow 57, Basic Red 76, Basic Blue 99, Basic Brown 16 and Basic Brown 17, and HC Blue 16, as well as Basic Yellow 87, Basic Orange 31, and Basic Red 51. Preferred nonionic substantive dyes are HC Yellow 2, HC Yellow 4, HC Yellow 5, HC Yellow 6, HC Yellow 12, HC Orange 1, Disperse Orange 3, HC Red 1, HC Red 3, HC Red 10, HC Red 11, HC Red 13, HC Red BN, HC Blue 2, HC Blue 11, HC Blue 12, Disperse Blue 3, HC Violet 1, Disperse Violet 1, Disperse Violet 4, and Disperse Black 9, as well as 1,4-diamino-2-nitrobenzene, 2-amino-4-nitrophenol, 1,4-bis-(2-hydroxyethyl)amino-2-nitrobenzene, 3-nitro-4-(2-hydroxyethyl)aminophenol, 2-(2-hydroxyethyl)amino-4,6-dinitrophenol, 4-[(2-hydroxyethyl)amino]-3-nitro-1-methylbenzene, 1-amino-4-(2-hydroxyethyl)amino-5-chloro-2-nitrobenzene, 4-amino-3-nitrophenol, 1-(2'-ureidoethyl)amino-4-nitrobenzene, 2-[(4-amino-2-nitrophenyl)amino]benzoic acid, 6-nitro-1,2,3,4-tetrahydroquinoxaline, 2-hydroxy-1,4-naphthoquinone, picramic acid and the salts thereof, 2-amino-6-chloro-4-nitrophenol, 4-ethylamino-3-nitrobenzoic acid, and 2-chloro-6-ethylamino-4-nitrophenol.

In addition, naturally occurring dyes such as those included, for example, in henna red, henna neutral, henna black, chamomile blossom, sandalwood, black tea, walnut, black alder bark, sage, logwood, madder root, catechu, and alkanna root, may also be used as substantive dyes.

The composition (M2) used in method step c) preferably also includes at least one substantive dye in an overall quantity of 0.001 to 10% by weight, preferably 0.01 to 8% by weight, more preferably 0.1 to 5% by weight, in particular 0.5 to 3% by weight, based on the total weight of the composition (M2).

The oxidation dye precursors (developer and coupler) themselves are not colored. The actual dyes are not formed until the oxidation dye precursors contact an oxidizing agent (preferably hydrogen peroxide). In a chemical reaction, the developer components used as oxidation dye precursors (such as p-phenylenediamine derivatives or p-aminophenol derivatives, for example) are converted, initially oxidatively, by hydrogen peroxide into a reactive intermediate stage, also referred to as quinone imine or quinone diimine, which in an oxidative coupling reaction then reacts with the coupler components to form the particular dye.

The compositions (M2) therefore additionally include one or more oxidizing agents that are different from atmospheric oxygen. Persulfates, peroxodisulfates, chlorites, hypochlorites, and in particular hydrogen peroxide and/or one of the solid addition products thereof with organic or inorganic compounds are suitable as oxidizing agent.

Methods preferred according to the invention are therefore characterized in that the composition (M2) used in method step c) includes at least one oxidizing agent from the group comprising persulfates, chlorites, hydrogen peroxide, and addition products of hydrogen peroxide with urea, melamines, and sodium borate.

Within the scope of the present invention, it is advantageous when the composition (M2) used in method step c) includes the at least one oxidizing agent in an overall quantity of 1.0 to 12% by weight, preferably 1.5 to 12% by weight, more preferably 2.0 to 12% by weight, particularly preferably 3.0 to 12% by weight, in particular 4.0 to 12% by weight, based on the total weight of the composition (M2). This quantity of oxidizing agent ensures on the one hand sufficient fixing of the shaped keratinic fibers, and on the other hand, the reaction of the used developer components and coupler components to form the desired dyes. If hydrogen peroxide and the solid addition products thereof are used as oxidizing agent, the above-mentioned overall quantity is calculated based on 100% $H_2O_2$.

Hydrogen peroxide is a particularly preferred oxidizing agent within the scope of the present invention. Preferred methods according to the invention are therefore characterized in that the composition (M2) used in method step c) as oxidizing agent includes hydrogen peroxide in an overall quantity of 0.5 to 15% by weight, preferably 1 to 12.5% by weight, more preferably 1.5 to 10% by weight, in particular 1.5 to 7.5% by weight, based on the total weight of the composition (M2). The above-mentioned overall quantity is calculated based on 100% $H_2O_2$.

To achieve an intensified lightening and bleaching effect, the composition (M2) may also include at least one peroxo salt. Suitable peroxo salts are inorganic peroxo compounds preferably selected from the group comprising ammonium peroxodisulfate, alkali metal peroxodisulfates, ammonium peroxomonosulfate, alkali metal peroxomonosulfates, alkali metal peroxodiphosphates, and alkaline earth metal peroxides, and the mixtures thereof. Peroxodisulfates, in particular ammonium peroxodisulfate, potassium peroxodisulfate, and sodium peroxodisulfate, are particularly preferred.

The above-mentioned peroxo salts are included in an overall quantity of 0.5 to 20% by weight, preferably 1 to 12.5% by weight, more preferably 2.5 to 10% by weight, in particular 3 to 6% by weight, based on the total weight of the composition (M2).

The coloring agent (M2) may also include at least one alkalizing agent for setting a basic pH. Setting a basic pH, using the at least one alkalizing agent, is necessary to ensure opening of the outer scaly layer (cuticle) and to allow penetration of the oxidation dye precursors into the hair.

Methods preferred according to the invention are therefore characterized in that the composition (M2) used in method step c) has a pH of pH 7.0 to pH 14.0, preferably pH 8.8 to pH 11.0, more preferably pH 9.0 to pH 10.8, in particular pH 9.2 to pH 10.5, at 20° C.

Organic alkalizing agents that are usable according to the invention are preferably selected from alkanolamines of primary, secondary, or tertiary amines with a $C_2$-$C_6$ alkyl base structure bearing at least one hydroxyl group. Alkanolamines very particularly preferred according to the invention are selected from the group comprising 2-aminoethan-1-ol (monoethanolamine), 2-amino-2-methylpropan-1-ol, and 2-amino-2-methyl-propane-1,3-diol, and the mixtures thereof. Monoethanolamine is a particularly preferred alkanolamine. Suitable basic amino acids are lysine, arginine, and ornithine. Inorganic alkalizing agents according to the invention are preferably selected from the group comprising sodium hydroxide, potassium hydroxide, calcium hydroxide, barium hydroxide, sodium phosphate, potassium phosphate, sodium silicate, potassium silicate, sodium carbonate, and potassium carbonate, and the mixtures thereof.

Methods particularly preferred according to the invention are therefore characterized in that the composition (M2) used in method step c) as an alkalizing agent includes at least one compound from the group comprising sodium hydroxide, potassium hydroxide, ammonia, monoethanolamine, 2-amino-2-methylpropane, and alkali and ammonium hydrogen carbonates.

In this regard, it is particularly preferred when the composition (M2) used in method step c) as an alkalizing agent includes ammonia. The occurrence of unpleasant odors during the oxidative dyeing, in particular lightening or dyeing, is thus avoided.

The alkalizing agents must be used in specific quantities in order to set a basic pH. According to the invention, the composition (M2) used in method step c) therefore advantageously includes the at least one alkalizing agent in an overall quantity of 0.1 to 15% by weight, preferably 0.5 to 12% by weight, more preferably 1.0 to 10% by weight, in particular 2.0 to 6.0% by weight, based on the total weight of the aqueous composition (M2).

The coloring agents (M2) may include further active ingredients and additives. It is therefore preferable within the scope of the present invention when the composition (M2) used in method step c) additionally includes at least one further compound selected from the group of (i) thickeners; (ii) linear or branched, saturated or unsaturated alcohols including 8 to 20 carbon atoms; (iii) surfactants, in particular nonionic surfactants; (iv) cationic polymers; and (v) the mixtures thereof.

The coloring agents (M2) are preferably formulated as flowable preparations. The coloring agents should be formulated in such a way that on the one hand they may be easily applied to and distributed on the application site, but on the other hand are sufficiently viscous that they remain at the site of action during the exposure period and do not run.

According to the invention, it has therefore proven advantageous when the composition (M2) used in method step c) includes at least one thickener from the group comprising (i) anionic synthetic polymers; (ii) cationic synthetic polymers; (iii) naturally occurring thickeners such as nonionic guar gums, scleroglucan gums, or xanthan gums, gum arabic, ghatti gum, karaya gum, tragacanth gum, carrageenan gum, agar-agar, locust bean gum, pectins, alginates, starch fractions and derivatives such as amyloses, amylopectin, and dextrins, and cellulose derivatives, for example methylcellulose, carboxyalkyl celluloses, and hydroxyalkyl celluloses; (iv) nonionic synthetic polymers such as polyvinyl alcohol or polyvinylpyrrolidinone; (v) inorganic thickeners, in particular phyllosilicates, for example bentonite, in particular smectites such as montmorillonite or hectorite; and (vi) the mixtures thereof, in an overall quantity of 0.0005 to 5.0% by weight, preferably 0.001 to 3.0% by weight, more preferably 0.005 to 1.0% by weight, in particular 0.008 to 0.01% by weight, based on the total weight of the composition (M2).

Within the scope of the present invention, it may be preferable for the linear or branched, saturated or unsaturated alcohol including 8 to 20 carbon atoms to be selected from the group comprising myristyl alcohol (1-tetradecanol), cetyl alcohol (1-hexadecanol), stearyl alcohol (1-octadecanol), cetearyl alcohol, 2-octyldodecanol, arachyl alcohol (eicosan-1-ol), gadoleyl alcohol ((9Z)-eicos-9-en-1-ol), arachidonic alcohol ((5Z,8Z,11Z,14Z)eicosa-5,8,11,14-tetraen-1-ol), preferably cetyl alcohol and/or cetearyl alcohol, and in an overall quantity of 1.0 to 35% by weight, preferably 5.0 to 30% by weight, more preferably 10 to 25% by weight, in particular 12 to 20% by weight, based on the total weight of the composition (M2).

The coloring agents (M2) may also preferably include at least one partial ester of a polyol including 2 to 6 carbon atoms and linear saturated carboxylic acids including 12 to 30, in particular 14 to 22, carbon atoms, whereby the partial esters may be hydroxylated, in an overall quantity of 0.5 to 10% by weight, in particular 3.0 to 8.0% by weight, based on the total weight of the composition (M2). Such partial esters are in particular the mono- and diesters of glycerin or the monoesters of propylene glycol or the mono- and diesters of ethylene glycol or the mono-, di-, tri-, and tetraesters of pentaerythrite, in each case with linear saturated $C_{12}$-$C_{30}$ carboxylic acids, which may be hydroxylated, in particular the esters with palmitic acid and stearic acid, the sorbitan mono-, di-, or triesters of linear saturated $C_{12}$-$C_{30}$ carboxylic acids, which may be hydroxylated, in particular the esters of myristic acid, palmitic acid, stearic acid, or mixtures of these fatty acids, and the methylglucose mono- and diesters of linear saturated $C_{12}$-$C_{30}$ carboxylic acids, which may be hydroxylated.

Within the scope of the present invention, it may be provided that the coloring agents (M2) include at least one polyol partial ester selected from glycerin monostearate, glycerin monopalmitate, glycerin distearate, glycerin dipalmitate, ethylene glycol monostearate, ethylene glycol monopalmitate, ethylene glycol distearate, ethylene glycol dipalmitate, and mixtures thereof, in particular mixtures of glycerin monostearate, glycerin monopalmitate, glycerin distearate, and glycerin dipalmitate, in an overall quantity of 0.5 to 10% by weight, in particular 3.0 to 8.0% by weight, based on the total weight of the composition (M2).

Furthermore, it may be provided according to the invention that the composition (M2) includes at least one surfactant. Within the meaning of the present invention, surfactants are amphiphilic (bifunctional) compounds composed of at least one hydrophobic and at least one hydrophilic molecular portion. A basic property of surfactants and emulsifiers is the oriented absorption to boundary surfaces, and the aggregation into micelles and the formation of lyotrophic phases.

According to one preferred embodiment of the present invention, the compositions (M2) used in method step c) include at least one nonionic surfactant in an overall quantity of 0.01 to 10% by weight, in particular 0.1 to 7.0% by weight, based on the total weight of the composition (M2).

The nonionic surfactant is preferably selected from the group of ethoxylated nonionic surfactants having an HLB value above 10, in particular above 13, esters of a carboxylic acid including 10 to 20 carbon atoms and a linear or branched alcohol including 1 to 10 carbon atoms, in particular decyl oleate, alkyl polyglucosides of formula $R^1O$-$[G]_p$, where $R^1$ stands for an alkyl and/or alkenyl functional group including 4 to 22 carbon atoms, G stands for a sugar functional group including 5 or 6 carbon atoms, and p stands for numbers from 1 to 10.

Ethoxylated nonionic surfactants having an HLB value above 10, in particular above 13, are included in the coloring agents (M2) preferably in an overall quantity of 0.5 to 6.0% by weight, in particular 1.0 to 4.0% by weight, based on the total weight of the composition (M2). To achieve the above-mentioned HLB values, the nonionic surfactant must have a sufficiently large ethoxylation number. In this regard, it is therefore advantageous for the ethoxylated nonionic surfactant to include at least 12 ethylene oxide units. In addition to the correspondingly ethoxylated alcohols, in particular lauryl alcohol, myristyl alcohol, cetyl alcohol, stearyl alcohol, arachyl alcohol, and behenyl alcohol, in particular the addition products of 20 to 60 of moles of ethylene oxide with castor oil and hydrogenated castor oil are particularly suitable according to the invention. The at least one ethoxylated nonionic surfactant is preferably selected from surfactants having the INCI names Ceteth-12, Steareth-12, Ceteareth-12, Ceteth-20, Steareth-20, Ceteareth-20, Ceteth-30, Steareth-30, Ceteareth-30, Oleth-7, Oleth-30, Ceteareth-50, PEG-40 Hydrogenated Castor Oil, and PEG-60 Hydrogenated Castor Oil, and mixtures of these substances, particularly preferably selected from Ceteareth-20 and Oleth-7.

Alkyl polyglycosides of formula $R^1O$-$[G]_p$ are included in the coloring agents (M2) preferably in an overall quantity of 0.01 to 1.0% by weight, in particular 0.1 to 0.5% by weight, based on the total weight of the composition (M2). The index number p in the above formula indicates the degree of oligeromerization (DP), i.e., the distribution of mono- and oligoglucosides, and stands for a number between 1 and 10. While p in a given compound must always be an integer, and may primarily assume the values p=1 through 6 here, the value p for a specific alkyl oligoglucoside is an analytically determined mathematical variable which usually represents a fractional number. Alkyl and/or alkenyl oligoglucosides having an average degree of oligeromerization p of 1.1 to 3.0 are preferably used according to the invention. From an application standpoint, alkyl and/or alkenyl oligoglucosides are preferred whose degree of oligeromerization is less than 1.7, in particular between 1.2 and 1.7. The alkyl or alkenyl functional group $R^1$ may be derived from primary alcohols including 4 to 20, preferably 8 to 16, carbon atoms. Very particularly preferred according to the invention are alkyl oligoglucosides based on hydrogenated $C_{12/14}$ coco alcohol having a DP of 1 to 3, as are commercially available, for example, under the INCI name "Coco Glucoside."

The aqueous composition (M2) may also include at least one cationic polymer. Suitable cationic polymers and their quantities have already been discussed in conjunction with the composition (M1). According to the invention, the composition (M2) used in method step c) particularly preferably includes as cationic polymer a polymer of N,N'-bis[3-(dimethylamino)propyl]urea and 1,1'-oxy-bis-(2-chloroethane) in an overall quantity of 0.01 to 0.5% by weight, based on the total weight of the composition (M2).

The composition (M3) used in method step e) is a fixative which fixes the keratinic fibers, situated on the deformation aids, in this shape. According to the invention, "fixing" is understood to mean the oxidation of the thiol groups of the keratin of the hairs to form disulfide groups.

The compositions (M3) therefore include one or more oxidizing agents that are different from atmospheric oxygen. Persulfates, peroxodisulfates, chlorites, hypochlorites, and in particular hydrogen peroxide and/or one of the solid addition products thereof with organic or inorganic compounds are suitable as oxidizing agents.

Methods preferred according to the invention are therefore characterized in that the composition (M3) used in method step e) includes at least one oxidizing agent from the group comprising persulfates, chlorites, hydrogen peroxide, and addition products of hydrogen peroxide with urea, melamines, and sodium borate.

Within the scope of the present invention, it is advantageous when the composition (M3) used in method step e) includes the at least one oxidizing agent in an overall quantity of 1.0 to 12% by weight, preferably 0.3 to 10% by weight, more preferably 0.5 to 7.0% by weight, particularly preferably 1.0 to 5.0% by weight, in particular 1.5 to 4.0% by weight, based on the total weight of the composition (M3). This quantity of oxidizing agent ensures sufficient fixing of the shaped keratinic fibers. If hydrogen peroxide and the solid addition products thereof are used as oxidizing agent, the above-mentioned overall quantity is calculated based on 100% $H_2O_2$.

Hydrogen peroxide is a particularly preferred oxidizing agent within the scope of the present invention. Preferred methods according to the invention are therefore characterized in that the composition (M3) used in method step e) as oxidizing agent includes hydrogen peroxide in an overall quantity of 0.3 to 10% by weight, preferably 0.5 to 7.0% by weight, particularly preferably 1.0 to 5.0% by weight, in particular 1.5 to 4.0% by weight, based on the total weight of the composition (M2). The above-mentioned overall quantity is calculated based on 100% $H_2O_2$.

The fixative (M3) may additionally include at least one acid for setting an acidic pH. Setting an acidic pH, using the at least one acid, is necessary to ensure the stability of the oxidizing agent used. Preferred acids are selected from dipicolinic acid, edible acids such as citric acid, acetic acid, malic acid, lactic acid, and tartaric acid, and diluted mineral acids such as hydrochloric acid, phosphoric acid, pyrophosphoric acid, and sulfuric acid, and mixtures thereof.

Methods preferred according to the invention are therefore characterized in that the composition (M3) used in method step e) has a pH of 1 to 7, preferably 1 to 6, in particular 2 to 6, at 20° C.

The fixative (M3) may additionally include at least one active substance and ingredient described in conjunction with the compositions (M1) and (M2). The fixative (M3) particularly preferably includes, in addition to the above-mentioned active substances and ingredients, at least one nonionic surfactant in the form of aminoxides, in particular dimethyl cocoalkylaminoxide, and at least one cationic surfactant of the quaternary ammonium compound, esterquat, or amidoamine type.

Preferred quaternary ammonium compounds are ammonium halides, in particular chlorides and bromides, such as alkyl trimethyl ammonium chlorides, dialkyl dimethyl ammonium chlorides, and trialkyl methyl ammonium chlorides, for example cetyl trimethyl ammonium chloride, stearyl trimethyl ammonium chloride, distearyl dimethyl ammonium chloride, lauryl dimethyl ammonium chloride, lauryl dimethyl benzyl ammonium chloride, and tricetyl methyl ammonium chloride, as well as the imidazolium compounds known under the INCI names Quaternium-27 and Quaternium-83. The long alkyl chains of the above-mentioned surfactants preferably include 10 to 18 carbon atoms.

Esterquats are known substances which include at least one ester function and at least one quaternary ammonium group as structural elements. Preferred esterquats are quaternized ester salts of carboxylic acids with triethanolamine, quaternized ester salts of carboxylic acids with diethanolalkylamines, and quaternized ester salts of carboxylic acids with 1,2-dihydroxypropyldialkylamines. Such products are marketed under the trade names Stepantex®, Dehyquart®, and Armocare®, for example. The products Armocare® VGH-70, an N,N'-bis(2-palmitoyloxyethyl)dimethyl ammonium chloride, and Dehyquart® F-75, Dehyquart®C-4046, Dehyquart® L80, and Dehyquart® AU-35 are examples of such esterquats.

Alkylamidoamines are usually prepared by amidation of natural or synthetic fatty acids and fatty acid cuts with dialkylaminoamines. The stearamidopropyldimethylamine commercially available under the name Tegoamid® S 18 represents a compound from this substance group that is particularly suitable according to the invention.

The cationic surfactants are preferably used in an overall quantity of 0.05 to 10% by weight, based on the total weight of the composition (M3). An overall quantity of 0.1 to 5% by weight, based on the total weight of the composition (M3), is particularly preferred.

The present invention is outlined in particular by the following items:

1. A method for the permanent shaping and color modification of keratinic fibers in a single process, the method comprising the following method steps in the stated sequence:
    a) applying an aqueous composition (M1), including at least one keratin-reducing compound and at least one alkalizing agent, to the keratinic fibers and leaving this composition (M1) on the keratinic fibers for a period of 5 to 50 minutes at a temperature of 20 to 45° C.,
    b) rinsing the keratinic fibers, and optionally drying the keratinic fibers using a towel and/or hair dryer,
    c) applying a composition (M2), including at least one oxidation dye precursor and at least one oxidizing agent, to the keratinic fibers and deforming the keratinic fibers, using deformation aids,
    d) allowing the composition (M2) applied in method step c) to act for 10 to 35 minutes,
    e) applying an aqueous composition (M3), including at least one oxidizing agent, to the keratinic fibers and leaving this composition (M3) on the keratinic fibers for 30 seconds to 15 minutes,
    f) rinsing the keratinic fibers with removal of the deformation aids, and
    g) optionally applying an aftertreatment agent to the keratinic fibers.

2. The method according to item 1, characterized in that a permanent wave is carried out as permanent shaping, and lightening or dyeing is carried out as color modification.

3. The method according to one of items 1 or 2, characterized in that the deformation aids used in method step a) have a diameter of 1 to 10 cm, preferably 1 to 8 cm, more preferably 1 to 6 cm, in particular 2 to 5 cm.

4. The method according to one of the preceding items, characterized in that the composition (M1) used in method step a) includes the at least one keratin-reducing compound in an overall quantity of 5 to 20% by weight, preferably 7 to 18% by weight, more preferably 9 to 16% by weight, in particular 10 to 15% by weight, based on the total weight of the aqueous composition (M1).

5. The method according to one of the preceding items, characterized in that the composition (M1) used in method step a) includes as alkalizing agent at least one compound from the group comprising sodium hydroxide, potassium hydroxide, ammonium hydroxide, ammonia, monoethanolamine, 2-amino-2-methylpropane, and alkyl and ammonium hydrogen carbonates.

6. The method according to item 5, characterized in that the composition (M1) used in method step a) includes sodium hydrogen carbonate and/or monoethanolamine as alkalizing agent.

7. The method according to one of the preceding items, characterized in that the composition (M1) used in method step a) includes the at least one alkalizing agent in an overall quantity of 0.1 to 15% by weight, preferably 0.5 to 12% by weight, more preferably 1.0 to 10% by weight, in particular 1.5 to 7% by weight, based on the total weight of the aqueous composition (M1).

8. The method according to one of the preceding items, characterized in that the composition (M1) used in method step a) has a pH of 5 to 12, preferably 5 to 10, in particular 5 to 9.5, at 20° C.

9. The method according to one of the preceding items, characterized in that the composition (M1) used in method step a) has a weight ratio of the keratin-reducing compound to the alkalizing agent of 1:200 to 1:1, preferably 1:50 to 1:1, more preferably 1:30 to 1:1, particularly preferably 1:20 to 1:1, in particular 1:10 to 1:1.

10. The method according to one of the preceding items, characterized in that the composition (M2) used in method step c) includes the at least one oxidation dye precursor in an overall quantity of 0.001 to 10% by weight, preferably 0.01 to 8% by weight, more preferably 0.1 to 5% by weight, in particular 0.5 to 3% by weight, based on the total weight of the composition (M2).

11. The method according to one of the preceding items, characterized in that the composition (M2) used in method step c) includes, as oxidizing agent, hydrogen peroxide in an overall quantity of 0.5 to 15% by weight, preferably 1 to 12.5% by weight, more preferably 1.5 to 10% by weight, in particular 1.5 to 7.5% by weight, based on the total weight of the composition (M2).

12. The method according to one of the preceding items, characterized in that the composition (M2) used in method step c) includes as alkalizing agent at least one compound from the group comprising sodium hydroxide, potassium hydroxide, ammonia, monoethanolamine, 2-amino-2-methylpropane, and alkali and ammonium hydrogen carbonates.

13. The method according to one of the preceding items, characterized in that the composition (M2) used in method step c) includes the at least one alkalizing agent in an overall quantity of 0.1 to 15% by weight, preferably 0.5 to 12% by weight, more preferably 1.0 to 10% by weight, in particular 2.0 to 6.0% by weight, based on the total weight of the aqueous composition (M2).

14. The method according to one of the preceding items, characterized in that the composition (M3) used in method step e) includes, as oxidizing agent, hydrogen peroxide in an overall quantity of 0.3 to 10% by weight, preferably 0.5 to 7.0% by weight, particularly preferably 1.0 to 5.0% by weight, in particular 1.5 to 4.0% by weight, based on the total weight of the composition (M2).

15. The method according to one of the preceding items, characterized in that the composition (M3) used in method step e) has a pH of 1 to 7, preferably 1 to 6, in particular 2 to 6, at 20° C.

The following examples are intended to explain preferred embodiments of the invention, without, however, limiting same.

EXAMPLES

1. Aqueous Composition (M1)—Waving Agent

The aqueous composition (M1) in the form of a waving agent was obtained by mixing the components listed below.

TABLE 1

Waving agent

| Raw material | Quantity (% by weight) |
|---|---|
| Natrosol HR 250[1] | 0.3 |
| Monoethanolamine thioglycolate, 83% | 18 |
| Monoethanolamine | 1.3 |
| Sodium hydrogen carbonate | 2.8 |
| HEDP, 60% | 0.1 |
| Plantacare 2000 UP[2] | 4.0 |
| Orange oil, sweet | 0.05 |
| Gluadin W 40 BP[3] | 0.1 |
| Polyquaternium-6 | 0.1 |
| Calendula KBA Herabsec[4] | 0.1 |
| Fragrance | 0.5 |
| Water | To make 100 |

[1]Natrosol HR 250 (INCI name: Hydroxyethylcellulose; Ashland)
[2]Plantacare 2000 UP (INCI name: Decyl Glucoside, Aqua (water); BASF)
[3]Gluadin W 40 BP (INCI name: Hydrolyzed Wheat Protein; BASF)
[4]Calendula KBA Herabsec (INCI name: Maltodextrin, Calendula Officinalis Flower Extract; Lipoid)

2. Oxidative Coloring Agent (M2)

The color cream described below in Table 2 was prepared, and immediately prior to application was in each case mixed in a 1:1 ratio with the oxidizing agent preparation 01 listed in Table 3:

| Raw material | Quantity (% by weight) |
|---|---|
| Carbopol 934[5] | 0.2 |
| Lanette E[6] | 0.8 |
| Genapol LRO liquid[7] | 4.8 |
| KOH, 50% | 0.17 |
| Edenor PK 1805[8] | 0.45 |
| Cutina GMS[9] | 4.4 |
| 2-Octyldodecanol | 2.2 |
| Cetearyl alcohol | 13.2 |
| Ceteareth-20 | 3.3 |
| Titanium dioxide | 0.5 |
| Sodium sulfite, anhydrous | 0.1 |
| Phospholipid EFA[10] | 0.1 |
| Tetrasodium EDTA | 0.2 |
| Merquat Plus 3330[11] | 1.5 |
| Ascorbic acid | 0.05 |
| Ammonia, 25% | 12 |
| Puricare LS 9658[12] | 1.0 |
| p-Toluylenediamine sulfate | 0.077 |
| Resorcinol | 0.042 |
| Fragrance | 0.4 |
| Water | To make 100 |

[5]Carbopol 934 (INCI name: Carbomer, Lubrizol)
[6]Lanette E (INCI name: Decyl Glucoside, Aqua (water); BASF)
[7]Genapol LRO liquid (INCI name: Sodium Laureth Sulfate; Clariant)
[8]Edenor PK 1805 (INCI name: Oleic Acid; Emery)
[9]Cutina GMS (INCI name: Glyceryl Stearate; BASF)
[10]Phospholipid EFA (INCI name: Linoleamidopropyl PG-Dimonium Chloride Phosphate PEG-60 Hydrogenated Castor Oil, Croda)
[11]Merquat Plus 3330 (INCI name: Polyquaterniuim-39; Lubrizol)
[12]Puricare LS 9658 (INCI name: Water, Glycerine, Moringa Pterygosperma Seed Extract; BASF)

TABLE 3

Oxidizing agent preparation O1

| Raw material | % by weight |
|---|---|
| Sodium benzoate | 0.04 |
| Dipicolinic acid | 0.1 |
| Disodium pyrophosphate | 0.1 |
| KOH, 50% | 0.2 |
| 1,2-Propanediol | 0.5 |
| HEDP | 0.25 |
| Paraffin oil | 2.0 |
| Lanette O[13] | 3.6 |
| Eumulgin B 2[14] | 1.2 |
| Hydrogen peroxide, 50% | 18.2 |
| Water | To make 100.0 |

[13]Lanette O (INCI name: Cetearyl Alcohol; BASF)
[14]Eumulgin B 2 (INCI name: Ceteareth-20, BASF)

3. Aqueous Composition (M3)—Fixative

The aqueous composition (M3) in the form of a fixative was obtained by mixing the components listed below.

TABLE 4

Fixative

| Raw material | % by weight |
|---|---|
| 50% NaOH | 0.1 |
| Polyquaternium-6 | 0.2 |
| Dehyquart A CA[15] | 0.3 |
| HEDP, 60% | 1.7 |
| Aromox MCD W[16] | 3.0 |
| Hydrogen peroxide, 50% | 4.0 |
| Water | To make 100.0 |

[15]Dehyquart A CA (INCI name: Aqua (water), Cetrimonium Chloride; BASF)
[16]Aromox MCD W (INCI name: Cocamine Oxide, Akzo Nobel)

4. Experimental Procedure and Evaluation of Results:

Undamaged hair was moistened with water and rubbed with a towel. The waving agent prepared according to item 1 was applied to the towel-dry hair, and left on the hair for an exposure time of 5 to 30 minutes. The hair was then rinsed with water having a temperature of 30° C. and optionally rubbed with a towel.

After rinsing out the waving agent, the oxidative coloring agent prepared according to item 2 was applied to the hair. A strand of hair was then divided off in the width of the curlers used, and combed out straight. The hair strand was centrally placed in a sheet of folded perm paper and wound onto curlers having a diameter of 2 to 5 cm in each case. This procedure was repeated until all the hair was wound on curlers. The oxidative coloring agent was left on the hair for an exposure time of 10 to 30 minutes.

For fixing, the fixative prepared according to item 3 was applied to the hair situated on the curlers, and left on the hair for an exposure time of 30 seconds to 10 minutes.

The hair was then rinsed with water having a temperature of 30° C., rubbed with a towel, and dried with a hair dryer.

A uniform waving and dyeing result was obtained, and the hair experienced very little or no damage due to the method according to the invention.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. A method for the permanent shaping and color modification of keratinic fibers in a single process, the method comprising the following method steps in the stated sequence:
    a) applying an aqueous composition (M1), including 5 to 20% by weight based on a total weight of (M1) of at least one keratin-reducing compound including monoethanolamine thioglycolate, and including 1.5 to 7% by weight based on a total weight of (M1) of at least one alkalizing agent including monoethanolamine and sodium hydrogen carbonate, to the keratinic fibers and leaving this composition (M1) on the keratinic fibers for a period of 5 to 30 minutes at a temperature of 20 to 45° C.,
    b) rinsing the keratinic fibers, and leaving the keratinic fibers damp with perceptible residual moisture so there are no dry keratinic fibers,
    c) applying a composition (M2), including 0.1 to 5% by weight based on a total weight of (M2) of at least one oxidation dye precursor comprising a developer type precursor that is p-toluylenediamine and comprising a coupler type precursor that is resorcinol, and 4.0 to 12% by weight, based on the total weight of the composition (M2) of at least one oxidizing agent comprising hydrogen peroxide, calculated based on 100% $H_2O_2$, to the damp keratinic fibers and deforming the keratinic fibers, using deformation aids,
    d) allowing the composition (M2) applied in method step c) to act for 10 to 35 minutes,
    e) applying an aqueous composition (M3), including 1.5 to 4.0% by weight, based on the total weight of the composition (M3) of at least one oxidizing agent comprising hydrogen peroxide, calculated based on 100% $H_2O_2$, to the keratinic fibers and leaving this composition (M3) on the keratinic fibers for 30 seconds to 15 minutes,
    f) rinsing the keratinic fibers with removal of the deformation aids, and
    g) optionally applying an after-treatment agent to the keratinic fibers.

2. The method according to claim 1, wherein the deformation aids used in method step c) have a diameter of 1 to 10 cm.

3. The method according to claim 1, wherein the composition (M1) used in method step a) further includes at least one compound selected from the group consisting of sodium hydroxide, potassium hydroxide, ammonia, and 2-amino-2-methylpropane.

4. The method according to claim 1, wherein the composition (M3) used in method step e) has a pH of 1 to 7 at 20° C.

5. The method according to claim 1, wherein the step of leaving the composition (M1) on the keratinic fibers for a period of 5 to 30 minutes occurs at room temperature.

6. The method according to claim 1, wherein the aqueous composition (M1) further includes a non-ionic surfactant comprising decyl glucoside in an amount of from 0.5 to 5% by weight, based on the total weight of the composition (M1).

7. The method according to claim 1, wherein the aqueous composition (M1) further includes orange oil in an amount of from 0.01 to 0.1% by weight, based on the total weight of the composition (M1).

8. The method according to claim 1, wherein the aqueous composition (M1) has a pH of from 5 to 9.5 at 20° C.

9. The method according to claim 1, consisting essentially of the method steps a)-f) in the stated sequence.

10. The method according to claim 1, consisting of the method steps a)-f) in the stated sequence.

11. The method according to claim 1, wherein the at least one keratin-reducing compound further includes at least one compound chosen from the group comprising thiolactic acid and cysteine, and the salts thereof.

12. The method according to claim 1, wherein the at least one keratin-reducing compound further includes at least one compound chosen from the group comprising thiomalic acid, phenylthioglycolic acid, mercaptoethanesulfonic acid, and the salts and esters thereof, cysteine, cysteine, Bunte salts and salts of sulfurous acid, alkali disulfites, hydrogen sulfites, magnesium, ammonium, or alkanolammonium salts based on a $C_2$-$C_4$ mono-, di-, or trialkanolamine, and sulfites as alkali, ammonium, or alkanolammonium salts based on a $C_2$-$C_4$ mono-, di-, or trialkanolamine.

13. The method according to claim 1, wherein the at least one oxidation dye precursor further includes a coupler type precursor that is 2-methylresorcinol, 2-amino-3-hydroxypyridine, 3-aminophenol, and the physiologically acceptable salts thereof and the mixtures thereof.

14. The method according to claim 1, wherein the aqueous composition (M3) includes an acid chosen from dipicolinic acid, citric acid, acetic acid, malic acid, lactic acid, tartaric acid, hydrochloric acid, phosphoric acid, pyrophosphoric acid, sulfuric acid, and mixtures thereof.

15. The method according to claim 1, wherein the step of leaving the composition (M1) on the keratinic fibers occurs for a period of 20 to 40 minutes.

16. The method according to claim 1, wherein the step of allowing the composition (M2) applied in method step c) to act occurs for 20 to 25 minutes.

17. A method for the permanent shaping and color modification of keratinic fibers in a single process, the method comprising the following method steps in the stated sequence:
- a) applying an aqueous composition (M1), including at least one keratin-reducing compound and at least one alkalizing agent, to the keratinic fibers and leaving this composition (M1) on the keratinic fibers for a period of 5 to 50 minutes at a temperature of 20 to 45° C.,
- b) rinsing the keratinic fibers, and leaving the keratinic fibers damp with perceptible residual moisture so there are no dry keratinic fibers,
- c) applying a composition (M2), including at least one oxidation dye precursor and at least one oxidizing agent, to the damp keratinic fibers and deforming the keratinic fibers, using deformation aids,
- d) allowing the composition (M2) applied in method step c) to act for 10 to 35 minutes,
- e) applying an aqueous composition (M3), including at least one oxidizing agent, to the keratinic fibers and leaving this composition (M3) on the keratinic fibers for 30 seconds to 15 minutes,
- f) rinsing the keratinic fibers with removal of the deformation aids, and
- g) optionally applying an after-treatment agent to the keratinic fibers.

18. The method according to claim 17, consisting essentially of the method steps a)-f) in the stated sequence.

19. The method according to claim 17, consisting of the method steps a)-f) in the stated sequence.

20. The method according to claim 17 wherein the aqueous composition (M1) includes 5 to 20% by weight based on a total weight of (M1) of at least one keratin-reducing compound including monoethanolamine thioglycolate, and includes 1.5 to 7% by weight based on a total weight of (M1) of at least one alkalizing agent including monoethanolamine and sodium hydrogen carbonate; and wherein the composition (M2) includes 0.1 to 5% by weight based on a total weight of (M2) of at least one oxidation dye precursor comprising a developer type precursor that is p-toluylenediamine and comprising a coupler type precursor that is resorcinol, and 4.0 to 12% by weight, based on the total weight of the composition (M2) of at least one oxidizing agent comprising hydrogen peroxide, calculated based on 100% $H_2O_2$.

* * * * *